United States Patent [19]
Felder, Jr. et al.

[11] Patent Number: 5,698,231
[45] Date of Patent: Dec. 16, 1997

[54] PESTICIDE SOLUTION

[76] Inventors: Thomas J. Felder, Jr.; Edward R. Felder, both of 1419 E. 77th Pl., Los Angeles, Calif. 90001-3013

[21] Appl. No.: 705,947

[22] Filed: Aug. 30, 1996

[51] Int. Cl.$^6$ .......................... A01N 37/02; A01N 37/06; A01N 59/00; A01N 65/00

[52] U.S. Cl. .......................... 424/715; 424/716; 424/717; 424/722; 424/195.1; 514/557; 514/558; 514/560; 514/574

[58] Field of Search .................................. 424/722, 195.1, 424/715–717; 514/558, 560, 574, 557

[56] References Cited

U.S. PATENT DOCUMENTS 5,030,658  7/1991  Salloum et al. .......................... 514/560

OTHER PUBLICATIONS

Hackh's Chemical Dictionary, McGraw–Hill, Inc., New York, 1969, p. 616.

JICST–EPLUS Abstract, accession No. 930728364, 1993.

Puritch, George S., "Pesticidal soaps and Adjuvants–What are they and How do they work," Proceedings of the 23rd Annual Mainland Horticultual Improvement Association Growers' Short Course, Feb. 1981, pp. 53–67.

*Primary Examiner*—John Pak

[57] ABSTRACT

A pesticide solution comprising a spray bottle including a mixture of lemon juice, cleaning soda, liquid soap and water incorporated into a spray bottle to be used to combat roaches, ants, fleas and the like without risking harm to humans and household pets.

1 Claim, No Drawings

PESTICIDE SOLUTION

BACKGROUND OF THE INVENTION

1. Field of the Invention

The present invention relates to a pesticide solution and more particularly pertains to exterminating roaches, ants, fleas and the like with a pesticide solution.

2. Description of the Prior Art

The use of pesticides is known in the prior art. More specifically, pesticides heretofore devised and utilized for the purpose of treating for insects are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,242,907 to Dawson discloses a pesticidal control.

U.S. Pat. No. 4,900,732 to Berenter discloses a method of treating American and oriental cockroaches.

U.S. Pat. No. 4,379,168 to Dotolo discloses pesticides containing D-limonene.

U.S. Pat. No. 4,384,002 to Stoller discloses an odorless, non-volatile formaldehyde for use as a pesticide.

U.S. Pat. No. 4,234,582 to Takahashi et al. discloses a trialkyl isocyanates used as pesticides.

U.S. Pat. No. 5,366,961 to Harrington discloses pesticidal products.

While these devices fulfill their respective, particular objective and requirements, the aforementioned patents do not describe a pesticide solution for exterminating roaches, ants, fleas and the like.

In this respect, the pesticide solution according to the present invention substantially departs from the conventional concepts and designs of the prior art, and in doing so provides an apparatus primarily developed for the purpose of exterminating roaches, ants, fleas and the like.

Therefore, it can be appreciated that there exists a continuing need for new and improved pesticide solution which can be used for exterminating roaches, ants, fleas and the like. In this regard, the present invention substantially fulfills this need.

SUMMARY OF THE INVENTION

In the view of the foregoing disadvantages inherent in the known types of pesticides now present in the prior art, the present invention provides an improved pesticide solution. As such, the general purpose of the present invention, which will be described subsequently in greater detail, is to provide a new and improved pesticide solution and method which has all the advantages of the prior art and none of the disadvantages.

To attain this, the present invention essentially comprises

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved pesticide solution which has all the advantages of the prior art pesticides and none of the disadvantages.

It is another object of the present invention to provide a new and improved pesticide solution which may be easily and efficiently manufactured and marketed.

It is a further object of the present invention to provide a new and improved pesticide solution which is of durable and reliable construction.

An even further object of the present invention is to provide a new and improved pesticide solution which is susceptible of a low cost of manufacture with regard to both materials and labor, and which accordingly is then susceptible of low prices of sale to the consuming public, thereby making such a pesticide solution economically available to the buying public.

Still yet another object of the present invention is to provide a new and improved pesticide solution which provides in the apparatuses and methods of the prior art some of the advantages thereof, while simultaneously overcoming some of the disadvantages normally associated therewith.

Even still another object of the present invention is to provide a new and improved pesticide solution for exterminating roaches, ants, fleas and the like.

Lastly, it is an object of the present invention to provide a new and improved pesticide solution comprising a spray bottle including a mixture of lemon juice, cleaning soda, liquid soap and water incorporated into a spray bottle to be used to combat roaches, ants, fleas and the like without risking harm to humans and household pets.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the descriptive matter in which the preferred embodiments of the invention are described.

DESCRIPTION OF THE PREFERRED EMBODIMENT

Specifically, the device relates to a the device consists of a pesticide solution for exterminating roaches, ants, fleas and the like. In its broadest context, lemon juice, cleaning soda, liquid soap and water. Such components are individually configured and correlated with respect to each other so as to attain the desired objective.

The process of the present invention begins with taking a one gallon container. One cup of lemon juice is added to the container. One cup of cleaning soda is next added to the container. The lemon juice and cleaning soda are then mixed within the container until foam dissolves. One cup of liquid soap is then added to lemon juice and cleaning soda mixture within the container. The liquid soap and the lemon juice and cleaning soap mixture are then stirred until foam dissolves. Water is next added to the container to fill the container to a volume of one gallon. The contents of the container are then heated to a predetermined temperature. The heated contents to are then allowed to cool. The mixed contents of the container are finally added to a spray bottle. The solution is then ready to be sprayed within the house to battle household roaches, fleas and ants without risking the health of humans or household pets.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A method of mixing a pesticide solution for exterminating roaches, ants, and fleas, the method comprising, in combination:

providing a one gallon container;

adding one cup of lemon juice to the container;

adding one cup of cleaning soda to the container;

stirring the lemon juice and cleaning soda until foam dissolves;

adding one cup of liquid soap to lemon juice and cleaning soda mixture within the container;

stirring liquid soap and the lemon juice and cleaning soda mixture until foam dissolves;

adding water to the container to fill the container to a volume of one gallon;

heating contents of the container;

allowing heated contents to cool; and adding mixed contents of the container to a spray bottle for spraying in concentrated areas.

* * * * *